United States Patent [19]

Degenhardt

[11] 4,259,249

[45] Mar. 31, 1981

[54] PREPARATION OF HYDROXYL ZWITTERIONIC COMPOUNDS

[75] Inventor: Charles R. Degenhardt, Cincinnati, Ohio

[73] Assignee: The Procter & Gamble Company, Cincinnati, Ohio

[21] Appl. No.: 48,203

[22] Filed: Jun. 13, 1979

[51] Int. Cl.³ .................. C07C 101/12; C09F 7/00
[52] U.S. Cl. .................. 260/404; 260/501.13
[58] Field of Search .................. 260/501.13, 404

[56] References Cited

U.S. PATENT DOCUMENTS

| 3,304,349 | 2/1967 | Shen | 260/501.13 |
|---|---|---|---|
| 3,468,937 | 9/1969 | Strack et al. | 260/501.13 |
| 3,504,024 | 3/1970 | Diehl et al. | 260/526 |
| 3,617,439 | 11/1971 | Chapman, Jr. | 260/501.13 |
| 3,755,435 | 8/1973 | Sundby | 260/404 |
| 3,822,344 | 7/1974 | Corker | 424/44 |
| 3,929,678 | 12/1975 | Laughlin et al. | 252/526 |
| 4,110,358 | 8/1978 | Braunworth | 260/404 |

OTHER PUBLICATIONS

Boots et al., J. of Pharmaceutical Sciences, 64, pp. 1262-1264 & 1949-1952, 1975.

*Primary Examiner*—Natalie Trousof
*Assistant Examiner*—G. T. Breitenstein
*Attorney, Agent, or Firm*—Jerry J. Yetter; Jack D. Schaeffer; Richard C. Witte

[57] ABSTRACT

A method of preparing hydroxyl substituted ammonio carboxylates comprising a single step of reacting an epoxy ester with a tertiary amine in aqueous alcohol, yielding directly said hydroxyl substituted ammonio carboxylates. The hydroxyl substituted ammonio carboxylates are useful as detersive surfactants and as oral anti-ulcer agents.

8 Claims, No Drawings

PREPARATION OF HYDROXYL ZWITTERIONIC COMPOUNDS

TECHNICAL FIELD

The instant invention relates to zwitterionic surfactant-type molecules. Zwitterionic surfactants, generally, comprise a lipophilic group, a cationic center and an anionic end group separated from the cationic center by a hydrocarbyl moiety.

The instant invention relates to a method for preparing hydroxyl substituted ammonio carboxylates characterized by desirably high solubilities in water, which make them useful detersive surfactants. The zwitterionics of this invention also exhibit biological activity and are useful for the oral treatment of ulcers.

Art disclosed processes of making hydroxyl substituted non-surfactant type ammoniocarboxylates involve the preparation of the hydroxyl ammoniocarboxylate esters and a separate process step of converting them into the hydroxyl substituted carboxylate compounds. The instant invention provides a convenient, single step method for making the hydroxyl-substituted surfactant-type zwitterionic compounds.

BACKGROUND ART

U.S. Pat. No. 3,929,678 issued Dec. 30, 1975 discloses long-chain zwitterionic compounds and a method of preparing them.

Sharon G. Boots and Marvin R. Boots, J. of Pharm. Scien. 64. 1262 disclose a four-step synthesis of carnitine compounds represented by the formula $$(CH_3)_3 \overset{\oplus}{N}CH_2\underset{\underset{OH}{|}}{C}CH_2CO_2HCl^{\ominus}$$

Sharon G. Boots and Marvin Boots (Ibid) p. 1949 disclose the method of synthesis of 4-dialkylamino-3 hydroxybutyric acid, hydrochloride analogs of carnitine, by treating tert-butyl 3,4-epoxybutyrate with an appropriate amine, or amino chloride in methanol followed by a mild hydrolysis.

Diehl, et al., U.S. Pat. No. 3,504,024, disclose phosphonio carboxylates prepared as follows: A suitable tertiary phosphine is reacted with ω-chloro or ω-bromo carboxylate and then the resulting mixture is saponified.

Copending applications of J. McGrady and Laughlin, Pharmaceutically Active Zwitterionic Surfactants, Ser. No. 960,974; J. L. Fu, Y. C. Fu, R. G. Laughlin, J. S. Widder, J. P. Brown, Zwitterionic Pharmaceutical Composition, Ser. No. 878,147 relate to zwitterionic compounds.

U.S. Pat. No. 3,822,344 discloses N-alkyl substituted derivatives of glycine or its homologues which can exist in the form of zwitterionics.

The hydroxyl-substituted zwitterionic compounds of the present invention are disclosed and claimed in the co-pending U.S. patent application of Degenhardt and Gosselink, Ser. No. 043,561, filed May 29, 1979.

DISCLOSURE OF INVENTION

The present invention encompasses a one-step process for preparing hydroxyl substituted ammonio carboxylates of the general formula $$R_1R_2R_3\overset{\oplus}{N}CH_2\underset{\underset{OH}{|}}{C}H(CH_2)_nCO_2^{\ominus}$$

where the integer, n, can be 0, or 2 and above, especially 2 to about 10. In the formula, substituents $R_1$, $R_2$, and $R_3$ are hydrocarbyl moieties, more fully defined hereinafter.

The method of preparing compounds of the foregoing type wherein n is 0 or 2 to about 10, and above, comprises the single step of reacting the appropriate epoxy esters with tertiary amine compounds, as illustrated by the reaction sequence hereinbelow.

$$R_1R_2R_3N + CH_2\overset{O}{\overset{\diagup\diagdown}{\text{———}}}CH(CH_2)_nCO_2R_4 \xrightarrow[\text{aq. EtOH}]{70\%}$$
$$R_1R_2R_3\overset{\oplus}{N}CH_2\underset{\underset{OH}{|}}{C}H(CH_2)_nCO_2^{\ominus}$$

wherein $R_4$ can be, for example, short chain alkyl, especially methyl, ethyl or propyl, preferably ethyl.

The reaction of the tertiary amine compound and the epoxy ester is conveniently and preferably carried out in 70% aqueous ethanol solution (although other aqueous/organic solvents can be used) and directly yields the hydroxyl substituted ammonio carboxylates. The resultant hydroxyl substituted ammonio carboxylates have been found to be very water-soluble. Indeed, those preferred surfactant-type hydroxy zwit compounds having a $C_{22}$, and higher, group as $R_1$ are soluble in water, whereas, for most surfactants, solubility is essentially nil at $C_{20}$, and higher.

BEST MODE

The preferred hydroxyl substituted ammonio hexanoates herein are represented by the general formula $$R_1R_2R_3N^{\oplus}CH_2CHOHCH_2CH_2CH_2CO_2^{\ominus}$$

wherein $R_1$, $R_2$, and $R_3$ are each hydrocarbyl moieties, with $R_1$ being preferably n-$C_{14}$ alkyl, and longer, especially about $C_{14}$–$C_{26}$, and $R_2$ and $R_3$ are each shorter chain alkyl (generally $C_1$ to $C_5$), with methyl being preferred.

For use as detersive surfactants, the most preferred hydroxyl substituted ammonio hexanoates comprise the lipophilic hydrocarbyl substituent, $R_1$, as $C_{12}$ to $C_{20}$ alkyl, preferably from n-$C_{14}$ to n-$C_{18}$ alkyl, and $R_2$ and $R_3$ are each methyl.

For use as oral anti-ulcer agents, the most preferred hydroxyl substituted ammonio hexanoates comprise hydrocarbyl substituent $R_1$ as n-$C_{14}$ alkyl through about n-$C_{20}$ alkyl, preferably from about $C_{14}$ to $C_{18}$ alkyl, and $R_2$ and $R_3$ are each methyl.

The preferred method of preparing the hydroxyl substituted ammoniocarboxylates herein comprises reacting the appropriate epoxy ester with any desired tertiary amine ($R_1R_2R_3N$). The reaction is most preferably carried out in a 70% aqueous ethanol solution to yield, directly, the hydroxyl-substituted ammonio carboxylates.

The epoxy esters used in the synthesis scheme are readily available and can be conveniently prepared as follows: An olefinic acid is esterified in its potassium salt form with ethyl iodide. The resulting ester product is then treated with m-chloroperbenzoic acid to form the epoxy ester. The epoxy ester is then ready for use in the reaction sequence described in detail, below.

The tertiary amine compounds ($R_1R_2R_3N$) used herein are readily available commercially and the methods of preparing the amines are well known and do not constitute part of this invention.

The following exemplifies the preparation and isolation of hydroxyl substituted ammonio carboxylates. The same method can be used to prepare any of the hydroxyl substituted zwitterionics of this invention. While the reaction stoichiometry is 1:1 in amine:epoxy ester, an excess of the relatively less expensive amine starting material can be used to help drive the reaction to completion and increase yields of the hydroxyl substituted zwitterionic products.

EXAMPLE I

To a solution of ethyl 4,5-epoxypentanoate (1.0 g, 6.94 mmol) in 16 ml 70% aq. EtOH was added $Et_3N$ (7.03 g, 69.4 mmol). The mixture was placed in an oil bath at 55°–60° C. and stirred for 24 hours before solvent was removed under vacuum. The residue was dissolved in $H_2O$ (10 ml) and washed with diethyl ether (3×10 ml). The aqueous layer was concentrated using $CH_3CN$ to azeotropically remove the final traces of $H_2O$, affording a light yellow oil which crystallized overnight under high vacuum. Stirring with hot, dry acetone followed by cooling overnight in a refrigerator produced white crystals which were isolated by filtration under argon. Drying under high vacuum afforded about 66% yield of the compound $(Et_3)_3N^{\oplus}CH_2CHOHCH_2CH_2CO_2^{\ominus}$.

EXAMPLE II

To a solution of ethyl 4,5-epoxypentanoate (0.500 g, 3.47 mmol) in 16 ml 70% aq EtOH was added tetradecyldimethylamine (8.36 g, 34.7 mmol). The mixture was stirred at 70° C. for 72 hr. Solvent removal produced crystals which were purified by recrystallization from hexane-EtOH. Drying under high vacuum afforded 857 mg (69%) of the desired product n-$C_{14}H_{29}N^{\oplus}(CH_3)_2CH_2CHOHCH_2CH_2CO_2^{\ominus}$ as white crystals.

EXAMPLE III

The following illustrates the method of preparing 5-hydroxy-6-(docosyldimethylammonio)hexanoate.

To a solution of ethyl 5,6-epoxyhexanoate (3.00 g) 19.0 mmol) in 50 ml 70% aq EtOH was added docosyldimethylamine (6.71 g, 19.0 mmol). The mixture was stirred at 80° C. for 42 hr. The solvent was removed under vacuum and the resulting crystals purified by recrystallization from hexane-EtOH. Drying under high vacuum afforded 5.70 g (62%) of the title compound as white crystals.

EXAMPLE IV

Following the method of Example III, the following amines are converted to the respective 5-hydroxy hexanoate compounds:

n—$C_{14}H_{29}N(CH_3)_2$; n—$C_{16}H_{33}N(CH_3)_2$;
n—$C_{18}H_{37}N(CH_3)_2$; n—$C_{20}H_{41}N(CH_3)_2$;
n—$C_{22}H_{43}N(CH_3)_2$; n—$C_{24}H_{49}N(CH_3)_2$;
n—$CH_{26}H_{53}N(CH_3)_2$; n—$C_{10}H_{21}N(C_2H_5)_2$;
n—$CH_{12}H_{25}N(C_3H_7)_2$; n—$C_{13}H_{27}N(CH_3)(C_4H_9)$;
n—$C_{15}H_{31}N(CH_3)(C_5H_{11})$; N,N-dimethylbenzyl amine;
$C_2H_4=C_3H_5N(CH_3)_2$; and n—$C_{12}H_{25}C_6H_4N(CH_3)_2$.

INDUSTRIAL APPLICABILITY

As stated hereinbefore, the instant hydroxyl substituted ammoniocarboxylates are prepared by reacting a tertiary amine with an epoxy ester.

The epoxy esters used herein can be conveniently prepared by the reaction sequence.

$$CH_2=CH(CH_2)_nCO_2H \xrightarrow[C_2H_5I]{KOH,EtOH} CH_2=CH(CH_2)_nCO_2Et$$

(I)

(I) + m-chloroperbenzoic acid ⟶

$$CH_2\overset{O}{\overset{\diagup \diagdown}{\text{———}}}CH(CH_2)_nCO_2Et$$

For example, a typical preparation of ethyl 4,5-epoxy-pentanoate is as follows:

4-Pentenoic acid (12.0 g, 0.120 mol) was dissolved in 200 ml of dry EtOH and KOH pellets (7.1 g, 0.126 mol) were added. The mixture was stirred at room temperature until homogeneous. Ethyl iodide (24.3 g, 0.156 mol) was added and the solution was refluxed for 48 hrs. The cooled solution was poured onto $H_2O$ (600 ml) and extracted with pentane (200 ml). The organic extract was washed with $H_2O$ (2×500 ml) and dried ($MgSO_4$). Solvent removal afforded 10.0 g (65%) of ethyl 4-pentenoate. From the ethyl 4-pentenoate the corresponding epoxy ester, ethyl 4,5-epoxy-pentanoate, is prepared as follows: ethyl 4-pentenoate (9.90 g, 77.3 mmol), and m-chloroperbenzoic acid (18.5 g, 92.8 mmol, 85% assay) were dissolved in 300 ml of $CH_2Cl_2$ and stirred for 18 hr in an oil bath at 50° C. The mixture was then filtered, washed with 10% $NaHSO_3$, saturated aqueous $NaHCO_3$(2X), and $H_2O$ (2X) before drying ($MgSO_4$). Concentration under slight vacuum at room temperature followed by distillation (32° C., 0.07 mm) afforded 6.1 g (55%) of the ethyl 4,5-epoxy-pentanoate.

The tertiary amine compounds useful in the preparation of the hydroxyl-substituted ammonio carboxylates are readily available commercially. The reaction sequence of the present invention appears to be a general one for tertiary amines. Accordingly, the tertiary amine compounds used herein can be cyclic, branched, unsaturated, heterosubstituted, etc. The amines herein can be conveniently represented by the general formula $R_1R_2R_3N$ wherein $R_1$, $R_2$, and $R_3$ are each hydrocarbyl moieties, or two R groups can be cyclized at the atom to form a hetero-ring. The substituents $R_1$, $R_2$, and $R_3$ can be all short chain alkyl groups containing from about 1 to about 5 carbon atoms, or more, or any one or more of the R groups (preferably, not more than one) can comprise a long chain hydrocarbyl substituent, including, for example, alkyl, alkenyl, aralkyl, alkaryl, etc. group containing from about 10 to about 50, or more, carbon atoms.

Generally, the reaction of the epoxy ester and the tertiary amine can be carried out at a mole ratio of about 1:1 in a closed system at a temperature of 50° C. to 95° C. The reaction time is usually from 1 to 72 hours, yielding from 50%–95% of the hydroxyl substituted ammoniocarboxylates.

The aqueous-organic reaction solvent preferred for use is 70% EtOH/30% $H_2O$, but other water/organic mixtures can be used; for example 60:40 methanol-water; 50:50 isopropanol-water; 80% EtOH/20% H₂O; water-acetone; water-dioxane, and the like.

The hydroxyl substituted ammonio carboxylates herein exhibit desirable cleansing properties on fabrics and hard surfaces and possess anti-ulcer activity when ingested orally, as illustrated by the following examples.

EXAMPLE V

A laundry detergent composition comprising the hydroxyl substituted zwitterionic detersive surfactants of the present invention is as follows.

| Ingredient | Percent by Weight |
|---|---|
| n-C$_{16}$H$_{33}$N(CH$_3$)$_2$CH$_2$CHOH(CH$_2$)$_3$CO$_2^\ominus$ | 12.5 |
| Sodium tallow alkyl sulfate | 5.0 |
| Sodium tripolyphosphate | 4.5 |
| Sodium citrate | 5.0 |
| Sodium nitrilotriacetate | 5.0 |
| Sodium sulfate | 65.0 |
| Moisture and minors | Balance |

The detergent composition of Example V is prepared by drying an aqueous slurry of the indicated ingredients. 17.5 Grams of the composition in 40 liters of wash water (ca 80° C.) is used to launder fabrics in a standard automatic washing machine. Excellent greasy and clay soil removal from a variety of fabric types is secured.

EXAMPLE VI

In the detergent composition of Example V, the n-C$_{16}$ hydroxyl substituted zwitterionic is replaced by an equivalent amount of the following compounds, respectively, and excellent fabric detergent compositions are secured: n—C$_{18}$H$_{37}$N$^\oplus$(CH$_3$)$_2$CH$_2$CHOH(CH$_2$)$_3$CO$_2^\ominus$; n—C$_{12}$H$_{25}$C$_6$H$_4$N$^\oplus$(CH$_3$)$_2$CH$_2$—CHOH(CH$_2$)$_3$CO$_2^\ominus$; n—C$_{20}$H$_{41}$N$^\oplus$(C$_2$H$_5$)$_2$CH$_2$CHOH(CH$_2$)$_2$CO$_2^\ominus$; and n—C$_{20}$H$_{41}$C$_6$H$_6$N$^\oplus$(CH$_3$)$_2$CH$_2$CHOH(CH$_2$)$_2$CO$_2^\ominus$.

EXAMPLE VII

A heavy-duty liquid disinfectant/detergent composition especially useful for hard surface cleaning is as follows.

| Ingredient | Percent by Weight |
|---|---|
| n-C$_{22}$H$_{45}$N$^\oplus$(CH$_3$)$_2$CH$_2$CHOH(CH$_2$)$_5$CO$_2^\ominus$ | 5.0 |
| Sodium C$_{11-13}$ alkylbenzene sulfonate | 2.0 |
| Pluronic* | 16.0 |
| Sodium carboxymethylcellulose | 0.75 |
| Perfume and color | 0.25 |
| Water | Balance |

*Commercial mixture of detersive nonionic surfactants.

The composition of Example VII is applied directly to floors, walls, etc., in a standard cleaning operation to provide desirable cleansing and disinfecting benefits.

As disclosed above, the compounds of the present invention also provide anti-ulcer effects to humans and lower animals when administered orally. Within the scope of sound medical judgment, the dosage of hydroxyl substituted zwitterionic surfactant will vary with the particular ulcer condition (gastric and duodenal) being treated, the severity of the condition, the manner and duration of treatment, and the specific compound employed. Single dosages conveniently range from about 25 mg to about 2000 mg per kilogram of body weight per day; preferably three to four 500–1000 mg doses per day, at mealtimes and bedtime are used.

For purposes of convenient oral administration the zwitterionic compounds of this invention can be formulated as capsules, tablets, chewable tablets, granules, and the like. For treatment of non-human animals, the zwitterionics can be incorporated in animal feed, feed supplements or feed concentrates.

The following illustrates the use of the present zwitterionics as oral anti-ulcer agents.

EXAMPLE VIII

| Ingredient | Amount |
|---|---|
| n-C$_{18}$H$_{37}$N$^\oplus$(CH$_3$)$_2$CH$_2$CHOH(CH$_2$)$_3$CO$_2^\ominus$ | 750 mg |

The composition of Example VIII is provided in the form of a gelatin capsule. Oral administration of 1–3 capsules at mealtimes substantially reduces duodenal ulceration in a patient in need of such treatment.

Results similar to those of Example VIII are secured when the C$_{18}$ zwitterionic is replaced by an equivalent amount of the corresponding n-C$_{14}$, n-C$_{16}$ and n-C$_{20}$ hydroxyl ammonio hexanoates, respectively.

As can be seen from the foregoing, compounds with integer n being 0 and from 2 to about 10, and higher, can be prepared in the manner disclosed. However, when n=1, i.e., using 3,4-epoxy-butanoic acid, a two-step process is required. First, 3,4-butenoic acid ester is epoxidized in the manner used herein. The epoxide is then opened with a tertiary amine hydrohalide and, thereafter, the ester group is hydrolyzed with base.

Of course, the compounds herein readily form hydrohalide salts (e.g. hydrochloride salts) and these are also encompassed by this invention.

What is claimed is:

1. A one-step process for directly preparing hydroxyl ammonio carboxylates of the general formula

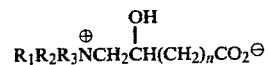

wherein R$_1$, R$_2$ and R$_3$ are each hydrocarbyl moieties and n is an integer which is 0 or 2 to about 10, comprising reacting an epoxy alkanoate ester of the formula

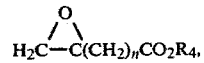

wherein n is as before, and R$_4$ is selected from a group consisting of methyl, ethyl and propyl hydrocarbyl groups with a tertiary amine of the formula R$_1$R$_2$R$_3$N in an aqueous organic reaction solvent, said process being carried out without a separate de-esterification step for removing R$_4$.

2. A process according to claim 1 wherein at least one of the moieties R$_1$, R$_2$ or R$_3$ is from about C$_1$ to about C$_{50}$ and wherein the remaining two hydrocarbyl moieties are each from about C$_1$ to about C$_5$.

3. A process according to claim 2 wherein at least one of the hydrocarbyl moieties, R$_1$, R$_2$, R$_3$, is a long-chain alkyl, alkenyl or alkaryl moiety comprising from about 10 to about 50 carbon atoms, with the remaining two hydrocarbyl moieties each comprising from about 1 to about 5 carbon atoms.

4. A process according to claim 1 wherein $R_4$ is an ethyl group.

5. A process according to claim 1 wherein n is an integer from 2 to about 10.

6. A process according to claim 5 wherein n is 2 or 3.

7. A process according to claim 1 wherein said aqueous-organic reaction solvent is an aqueous-alcohol solution.

8. A process according to claim 7 wherein said aqueous-organic reaction solvent is an aqueous ethanol solution.

* * * * *